(12) United States Patent
Shinde et al.

(10) Patent No.: US 8,132,467 B2
(45) Date of Patent: Mar. 13, 2012

(54) APPARATUS AND METHOD FOR MONITORING WEAR OF COMPONENTS

(75) Inventors: Sachin R. Shinde, Oviedo, FL (US); Anand A. Kulkarni, Oviedo, FL (US); David J. Mitchell, Oviedo, FL (US)

(73) Assignee: Siemens Energy, Inc., Orlando, FL (US)

( * ) Notice: Subject to any disclaimer, the term of this patent is extended or adjusted under 35 U.S.C. 154(b) by 316 days.

(21) Appl. No.: 12/194,876

(22) Filed: Sep. 15, 2008

(65) Prior Publication Data
US 2010/0068508 A1 Mar. 18, 2010

(51) Int. Cl.
*G01L 1/00* (2006.01)

(52) U.S. Cl. .......................................................... 73/774

(58) Field of Classification Search ................... 73/774, 73/777
See application file for complete search history.

(56) References Cited

U.S. PATENT DOCUMENTS

| | | | | |
|---|---|---|---|---|
| 4,024,617 A * | 5/1977 | McCormick | ................ | 148/526 |
| 4,626,476 A * | 12/1986 | Londry et al. | ................ | 428/457 |
| 4,812,050 A | 3/1989 | Epstein et al. | | |
| 5,164,247 A * | 11/1992 | Solanki et al. | ................ | 428/213 |
| 5,297,438 A * | 3/1994 | Alles et al. | ................ | 73/727 |
| 5,770,270 A * | 6/1998 | Lalezari et al. | ................ | 427/404 |
| 6,302,318 B1 * | 10/2001 | Hasz et al. | ................ | 228/254 |
| 6,485,678 B1 * | 11/2002 | Liang et al. | ................ | 420/37 |
| 6,620,456 B2 * | 9/2003 | Blanton et al. | ................ | 427/226 |
| 6,797,335 B1 * | 9/2004 | Paderov et al. | ................ | 427/530 |
| 6,838,157 B2 | 1/2005 | Subramanian | | |
| 7,004,622 B2 * | 2/2006 | Hardwicke et al. | ............ | 374/141 |
| 7,270,890 B2 | 9/2007 | Sabol et al. | | |
| 7,618,712 B2 * | 11/2009 | Sabol et al. | ................ | 428/469 |
| 2004/0006258 A1 | 1/2004 | Meyer et al. | | |
| 2004/0101022 A1 | 5/2004 | Hardwicke et al. | | |
| 2004/0202886 A1 | 10/2004 | Subramanian | | |
| 2005/0198967 A1 | 9/2005 | Subramanian | | |

FOREIGN PATENT DOCUMENTS

| | | |
|---|---|---|
| EP | 0158106 A1 | 12/2000 |
| WO | 2004067225 A1 | 8/2004 |
| WO | 2006007056 A1 | 9/2009 |

* cited by examiner

*Primary Examiner* — Lisa Caputo
*Assistant Examiner* — Octavia Davis

(57) ABSTRACT

A structure and method for instrumenting a component for monitoring wear in a coating. The method includes depositing a first thin layer of electrically insulating material, depositing a thin electrically conductive layer over the first electrically insulating layer, depositing a second thin layer of electrically insulating material over the electrically conductive layer. An overlying thickness of the coating material is deposited over the second thin layer of electrically insulating material. The thicknesses of the insulating and conducting layers is controlled to be small enough such that the overlying coating surface exposed to mechanical wear retains a desired degree of smoothness without the necessity for a separate planarization step.

15 Claims, 3 Drawing Sheets

APPARATUS AND METHOD FOR MONITORING WEAR OF COMPONENTS

STATEMENT REGARDING FEDERALLY SPONSORED DEVELOPMENT

Development for this invention was supported in part by Contract No. 70NANB4H3042, Conformal Direct Write Technology Enabled Wireless Smart Turbine Components, issued by the National Institute of Standards and Technology. Accordingly, the United States Government may have certain rights in this invention.

FIELD OF THE INVENTION

The present invention generally relates to monitoring wear of components of a machine such as an engine, and in particular to an improved apparatus and method for monitoring wear of components within an operating environment such as within a gas turbine engine.

BACKGROUND OF THE INVENTION

When two or more components of an engine come into contact with one another during operation of the engine, abrasion and wear of these components will occur. Also, relative motion between abutting components due to vibration will contribute to abrading action on the components. Moreover, the extremely high operating temperatures within an engine may exacerbate the wear problem. Wear of engine components can adversely impact the proper functioning of the engine. Component wear may be controlled in most applications by known methods such as lubricants, choice of materials, design features that limit motion, geometry of the components, and others. However, relative motion between components cannot be eliminated altogether and wear remains a reality for engine designers.

Prior to the occurrence of a structural or functional failure caused by wear, the suitability of components for continued service is typically determined by visual or dimensional inspection. However, there are many applications where regular inspections are not feasible because of factors including time, labor and/or disruptions due to down time. Thus, there is a need for monitoring the wear of a component while the component is in operation or without having to remove the component from its operational position.

BRIEF DESCRIPTION OF THE DRAWINGS

The invention is explained in the following description in view of the drawings that show.

DETAILED DESCRIPTION OF THE INVENTION

Figure 1:
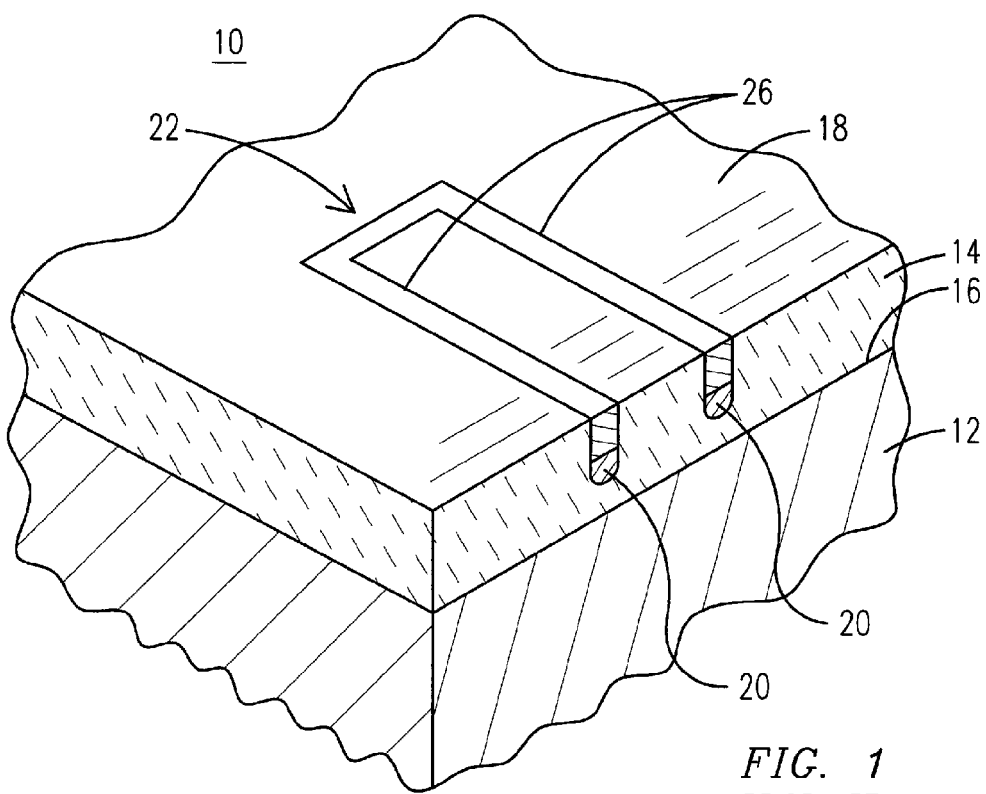
FIG. 1 is a perspective view of a prior art wear sensor embedded into the wear coating of a turbine component.

The present inventors have realized that it would be advantageous to use functional materials as sensors for wear monitoring in portions of a gas turbine engine and to embed such sensors in the wear coating of individual components of the engine. Components that may benefit from such embedded sensors include compressor diaphragms, airfoils, vanes, casings and blade rings in which vibrations and dynamic forces cause wear. Use of embedded wear sensors in such critical components of a gas turbine will reduce maintenance costs by facilitating the monitoring of component wear before it becomes critical and before it causes damage to the component, thereby preventing unscheduled outages.

Wear sensors can provide for real-time monitoring of component condition during operation of turbine engines. Knowing the condition of components in a turbine has many benefits, including condition-based maintenance. Significant reductions in operating costs may result as a consequence of advanced knowledge of a degrading condition of a turbine component. The present inventors have realized that thin film sensor technology may be used to deposit electrical circuits and elements thereof directly onto the surface of turbine components, thereby enabling the placement of wear sensors in locations not previously utilized and/or to achieve surface geometries above an embedded sensor that were not previously obtainable or were obtained only with more expensive processes.

As will be disclosed herein, thin film sensor technology allows the depositing of electrical circuits into coatings in conformal surfaces, such as compressor diaphragms or airfoils. The components manufactured with the techniques disclosed herein will have a smooth top surface and include wear sensors embedded therein. Hence, the prior art process steps of trenching and planarization may be omitted, which also avoids the possibility of damage to the wear coating caused by the planarization step.

The disclosed technique includes using thin film deposition technology to place electrical circuits directly onto the components and further using wireless technology to transmit data relevant to the status of the monitored component, thereby providing real-time usage data. The embedded functional component of the sensor and interconnect lines may be deposited on the component by means of plasma spraying, electron beam physical vapor deposition (EB PVD), chemical vapor deposition (CVD), pulsed laser deposition, mini-plasma, cold spray, direct-write, mini-high velocity oxyfuel, or solution plasma spraying, for example. Materials with functional properties (resistance and dielectric or insulating properties) are chosen in order to achieve optimal sensor system functionality and integrity, but without hindering the functionality of the instrumented component. The sensor system can be deposited directly onto the substrate surface prior to the deposition of a wear coating, or it may be embedded within the wear-resistant coating at one or more desired depths in order to monitor the wear rate of the component coating.

The conductive nature of the metallic component and also the wear-resistant coating requires an insulating layer to electrically isolate the sensor circuit from the component substrate and wear coating material. The initial step is to deposit an insulating layer on the surface. This material may be an oxide ceramic material that has high dielectric/insulating properties. The thickness of this ceramic layer is important, both from the view of insulation and sensor thickness. A thicker layer will cause undesired unevenness on the contact surfaces. A ceramic thickness range of 25 to 100 microns is desired, with a minimal thickness of 25 microns being desired for adequate electrical insulation. Since most components are made of iron or nickel based alloys, thermal expansion mismatch also becomes important at higher operating temperatures, therefore it is desired to match, as close as possible, the coefficient of thermal expansion of the various materials of the individual layers. However, because the layers are controlled to a desired degree of thinness, the stress effects of differential thermal expansion are somewhat mitigated, thereby allowing for some mismatch between the coefficients of thermal expansion. Depending upon the operating temperature, materials for the insulating layer may be a magnesium aluminum oxide (spinel) with a coefficient of thermal expansion (CTE) of approximately 7 micron/meter within the range of 0° C. up to 700° C.; or a yttria stabilized zirconia (YSZ) with a CTE of approximately 10 micron/meter between 500° C. and 800° C.

Following deposition of the insulating layer, a thin metallic conducting sensor layer, such as nickel chromium, is then deposited over the insulating layer. Again, a thickness of this conducting layer is important for achieving both functionality and the desired continuity and smoothness of the overlying top surface. A sensor having a thickness within the range of 5 to 25 microns may be desired, with the thickness being held as low as practical while achieving the desired functionality, such as a thickness of 5-20 microns or about 5 microns. Following deposition of the thin film metallic sensor, a second insulating layer is deposited over the sensor. The material and thickness requirement for the second insulating layer is the same as that for the initial insulating layer (i.e., at least or about 25 microns). The above-mentioned materials and specified thicknesses have been found to provide smooth top surfaces and also to provide the desired system integrity during operation.

Referring now to the drawings and to FIG. 1 in particular, a partial perspective view of a prior a technique of trenching for embedding wear sensors in the wear coating over the turbine components is shown. Component 10 is formed of a substrate material 12 having a barrier coating such as a layer of thermal barrier coating 14 disposed on one surface 16. The component 10 may be part of a gas turbine engine, or any other type of engine, wherein a base material must be protected from a harsh environment by a layer of a barrier material. In an embodiment, component 10 may be an airfoil member, such as a turbine blade disposed in the hot gas flow path of an engine, which component may typically be made of a super alloy material 12 with an oxide or non-oxide ceramic based overlaying thermal barrier coating 14.

Component 10 may alternatively be fabricated from a ceramic matrix composite (CMC) substrate coated with an environmental barrier coating (EBC) or a thermal barrier coating (TBC). Because the integrity of the coating 14 is critical to the overall integrity of the component 10, it is useful to obtain operating parameter information that directly affects the performance of the coating 14. Such information is obtained by embedding a sensor below the exposed surface 18 of the coating 14. The sensor may comprise electrical conductors 20 located below the surface 18 in the sensing location indicated generally by numeral 22.

The sensor may be one that provides a signal indicative of changes in resistance of the conductor 20 as a function of wear of the component 10. For example, as the coating 14 is worn away by abrasion during operation, a rut or groove is cut down to the conductor 20. The resistance of the conductor changes as it wears away, which may be sensed via appropriate circuitry known in the art. As the conductor is further worn away to the point of being severed, that is it is no longer a conductor, a signal is generated by the sensor indicative of a problem. Additional electrical conductors (not shown) may also be located below surface 18 for routing the signal produced by the sensor away from sensing location 22 to a termination location indicated generally by numeral 24 where they can conveniently exit the component 10. These additional electrical conductors may function for routing a signal from a sensor to a transmitter for transmission by a wireless telemetry system. The sensor and the conductors may be insulated from the surrounding environment by a layer of insulating material 26.

Figure 2:
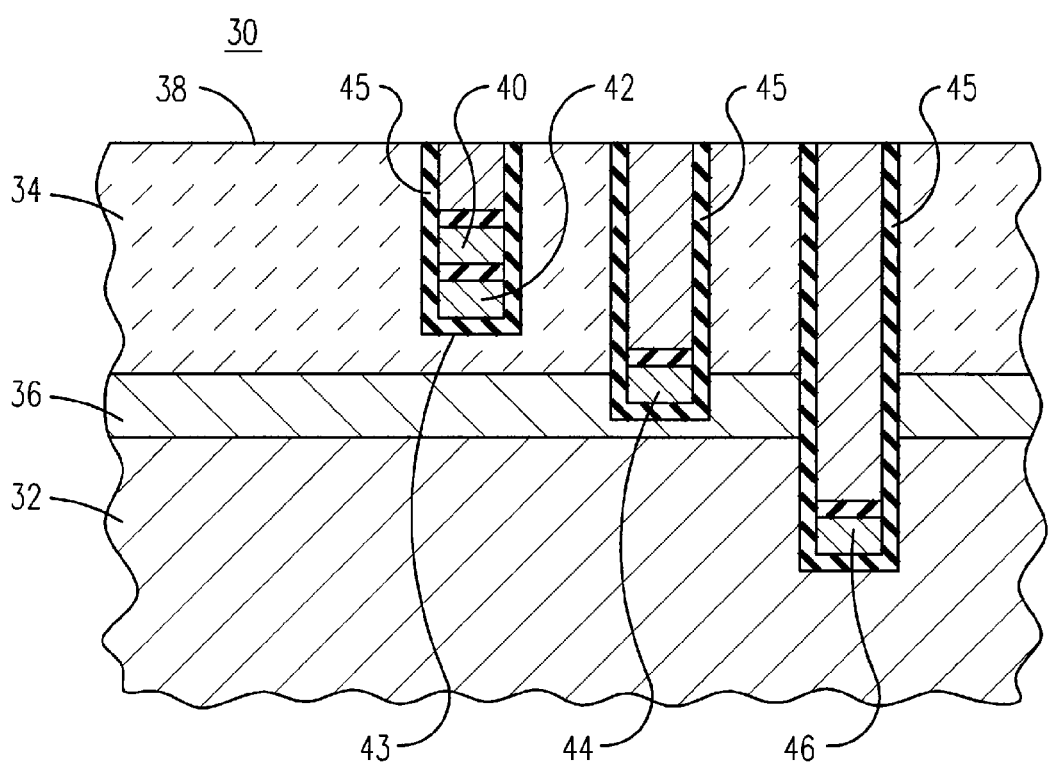
FIG. 2 is a cross-sectional view of a prior art technique of trenching for embedding wear sensors.

The sensors themselves may be multi-layered and may contain a combination of electrodes, as shown in FIG. 2, which is a partial cross-sectional view of another prior art technique of trenching for embedding wear sensors in the wear coatings over the turbine components and into the turbine components as well. Component 30 has a substrate material 32 covered by a barrier coating such as a layer of a thermal barrier coating material 34 for use in a very high temperature environment. As is known in the art of TBC coatings, a bond coat 36 such as MCrAlY material may be deposited on the substrate 32 prior to the application of the TBC material 34 to improve the adherence of the coating 34 to the substrate 32. Component 30 may be instrumented by a plurality of sensors embedded at a plurality of depths below a surface 38 of the TBC material 34 that is exposed to the external environment. A first sensor 40 is deposited in relatively shallow trench 43. Trench 43 may be lined with an electrically insulating coating 45 such as aluminum oxide to prevent the grounding of the sensor 40 to the TBC material 34. In accordance with the disclosed embodiment, sensor 40 may take any form known in the art, for example an ohmmeter measuring changes in resistance of embedded conductors 40, 42, 44 and 46.

Figure 3:
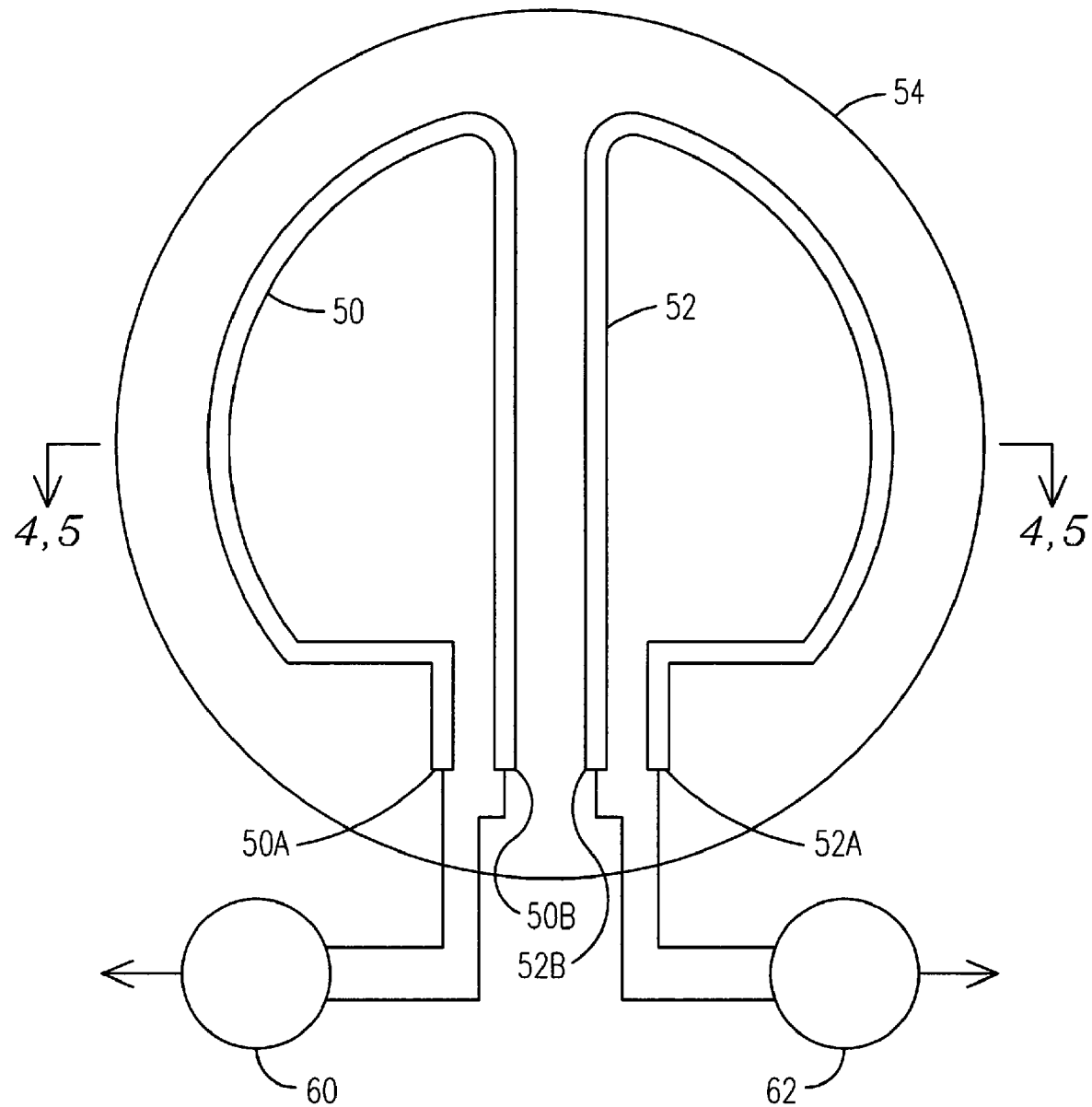
FIG. 3 is a plan view of a wear sensor conductor layout disposed across a turbine component to be monitored in accordance with one aspect of the invention.
Figure 5:
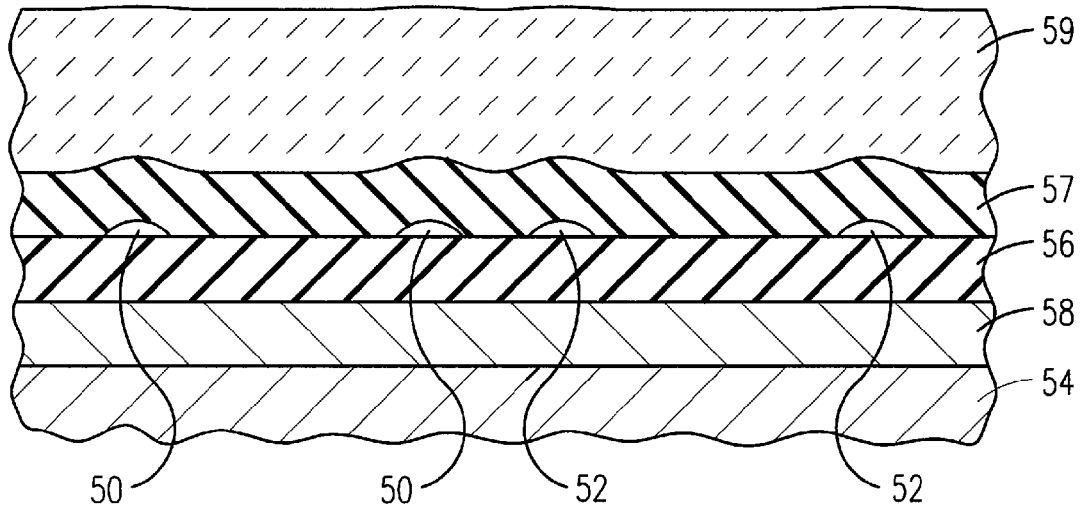
FIG. 5 is a cross-sectional view taken across the component shown in FIG. 3 illustrating the technique of constructing wear sensors in accordance with an aspect of the present invention without trenching and without the need for the process step of planarization.

Referring now to FIG. 3, a plan view of a pair of wear sensor conductors 50, 52 disposed across a turbine component 54 to be monitored for wear is shown. Each of the conductors 50, 52 are embedded between insulating layers 56 and 57, as illustrated in FIG. 5, and this structure is disposed between wear resistant coatings 58 and 59 deposited over the component 54. According to an illustrated embodiment, ends 50A, 50B of the conductor 50 are coupled to a measuring implement, such as a meter 60; and, the output of the meter 60 is coupled to a wireless transmitter (not shown) but as more fully disclosed in published U.S. Patent Application No US 2005/019867 A1 entitled SMART COMPONENT FOR USE IN AN OPERATING ENVIRONMENT, incorporated by reference herein. In a similar manner, ends 52A and 52B are coupled to a similar measuring implement 62; and, the output of the meter 62 is also coupled to a similar wireless transmitter (also not shown). In accordance with one embodiment, the meters 60 and 62 may be ohmmeters disposed for measuring the resistance of the respective conductors and detecting changes in resistance as the conductors are worn.

Figure 4:
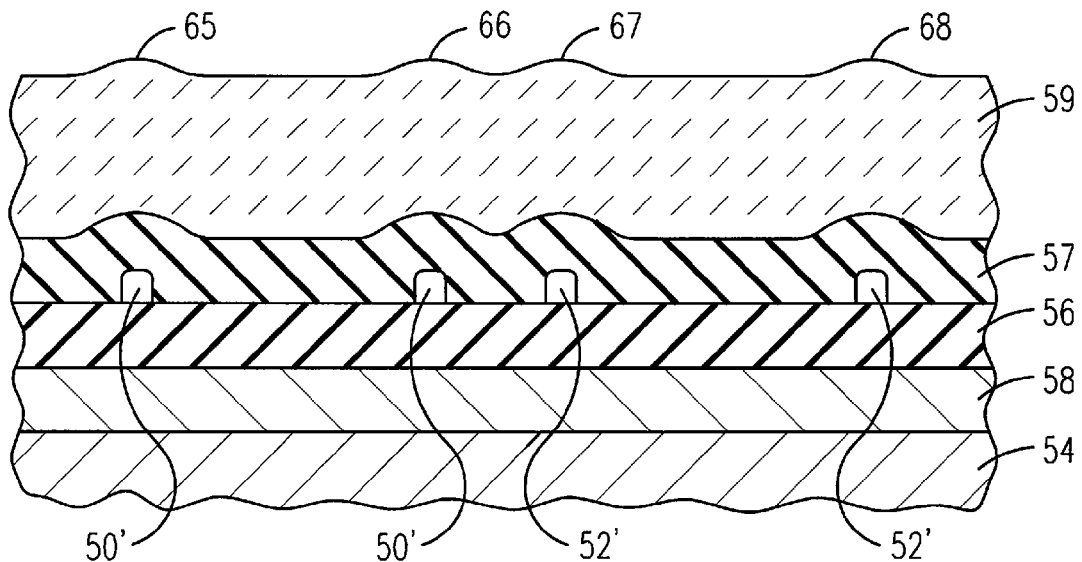
FIG. 4 is a cross-sectional view of a component illustrating yet another prior art technique of constructing wear sensors on the top of the component without the use of trenching, which requires the process step of planarization.

Referring now to FIG. 4, another prior art technique of embedding conductors in coatings is shown in a cross-sectional view. A first thermal barrier coating 58 is deposited on the surface of a component 54. The coating 58 may be a material identified as T-800, which is typically made of nickel chromium carbide. Next, an electrically insulating layer 56 is deposited over the layer 58. The conductors 50' and 52' are next deposited in a pattern across the component 54. In the prior art, these conductors were large in cross section with sharp vertical edges, similar to that shown in FIG. 4, such as may be formed by a masking process. After the subsequent coating layers 57, 59 are deposited over the conductors 50' and 52', bumps 65, 66, 67, 68 would translate to the top surface. It was then necessary to planarize the top surface by a mechanical wearing process. This additional step was time consuming and often caused cracks in the underlying material. Moreover, planarizing of a curved surface was problematic. As a result, prior art wear sensors were not applied in some locations, or they were applied with a resulting adverse affect on the overlying coating, or they were applied with expensive trenching steps.

Referring again to FIG. 5, a cross-sectional view taken across the component shown in FIG. 3 illustrating the technique of constructing wear sensors in accordance with one aspect of the present invention is shown. Importantly, the technique of the present invention does not require the process steps of trenching or planarization. A layer 58 of a coating material such as T800 material is first deposited over the surface of component 54. Next, an electrically insulating layer 56, such as magnesium aluminum oxide (spinel) is deposited over the layer 58, and is limited in thickness to between 25 and 100 microns, with 25 microns being preferred. The conductors 50 and 52 are next deposited on the layer 56. In accordance with the teachings of the present invention, these conductors are limited in thickness to between 5 and 25 microns, with 5 microns being preferred. After this, another insulating layer 57 is deposited over the conductors 50 and 52, and again the thickness of this layer 57 is limited to between 25 and 100 microns with 25 microns being preferred. Layers 56 and 57 may be of the same material or may be a different material selected to provide a particular complementary benefit, such as having a slightly different coefficient of thermal expansion in order to provide a graduated stress pattern.

In accordance with one embodiment of the invention, layer 58 is approximately 89 microns thick, while the layer 56 is approximately 36 microns thick, conductor 50, 52 is approximately 18 microns thick at its thickest point and being generally dome shaped as is commonly formed by known deposition techniques described above, the layer 57 is approximately 25 microns thick, and the top layer 59 is approximately 56 microns thick. The present invention provides an embedded wear sensor formed to have a total thickness, including the sensor conductor and associated insulating layers, that is limited to no more than a thickness such that an overlying thickness of coating material can be deposited to have a desired degree of top surface planarity without the need for a separate planarization step. It will be recognized that the terms "planar" and "planarity" and such are used herein to include both truly planar, flat surfaces, as well as smoothly curved surfaces wherein the terms are meant to incorporate the desired degree of smooth curvature without undesirable bumps in the surface.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A component comprising:
   a substrate material;
   a layer of wear resistant coating material deposited on a surface of the substrate material defining a surface exposed to mechanical wear;
   a layer of electrically conductive material disposed within the layer of wear resistant coating material and operative as a sensor when connected to a circuit, the layer of conductive material comprising a thickness of less than 25 microns;
   layers of electrically insulating material surrounding the layer of conductive material within the coating material, the layers of electrically insulating material comprising thicknesses of less than 100 microns above and less than 100 microns below the layer of conductive material; and,
   wherein the thickness of the layer of electrically conductive material is up to 22% of a combined thickness of the layer of insulating material and layer of wear resistant coating material disposed over the layer of electrically conductive material such that the surface exposed to mechanical wear retains a desired degree of smoothness without the necessity for a planarization of the surface.

2. The component of claim 1, wherein the layer of electrically conductive material comprises a thickness of 5-20 microns.

3. The component of claim 1, wherein the layer of electrically conductive material comprises a thickness of about 5 microns.

4. The component of claim 1, wherein the layer of electrically insulating material comprises a thickness of about 25 microns.

5. The component of claim 1, wherein the layer of coating material comprises T800 material and the layer of electrically insulating material comprises magnesium aluminum oxide or yttria stabilized zirconia.

6. The component of claim 1, wherein the layer of electrically conductive material comprises nickel chromium.

7. The component of claim 1, wherein the layer of electrically insulating material above the layer of electrically conducting material comprises a material different than the layer of electrically insulating material below the layer of electrically conducting material.

8. The component of claim 1 wherein the layer of electrically insulating material comprises one having a coefficient of thermal expansion of 7 microns per meter within the temperature range of 0° C. to 700° C.

9. The component of claim 1 wherein the layer of electrically insulating material comprises one having a coefficient of thermal expansion of 10 microns per meter within the temperature range of 500° C. to 800° C.

10. A method of making a structure for monitoring mechanical wear of a coated component, the method comprising:
    depositing a first wear resistant coating layer over a substrate to be protected from and monitored for wear;
    depositing a first layer of electrically insulating material over the first wear resistant coating layer;
    depositing an electrically conductive layer over the first electrically insulating layer;
    depositing a second layer of electrically insulating material over the electrically conductive layer;
    depositing a second wear coating layer over the second thin layer of electrically insulating material; and,
    controlling relative thicknesses of the respective layers wherein the thickness of the layer of electrically conductive material is up to 22% of the combined thickness of the layer of insulating material and layer of wear resistant coating material disposed over the layer of electrically conductive material such that a top wear surface of the structure retains a desired degree of smoothness without the necessity for a planarization step following the step of depositing a second wear coating.

11. The method as in claim 10, wherein the wear resistant coating layers comprise T800, and the electrically insulating layers are each deposited at a thickness of less than 100 microns.

12. The method as in claim 10, wherein the electrically insulating layers comprising magnesium aluminum oxide or yttria stabilized zirconia and are each deposited at a thickness of less than 100 microns.

13. The method as in claim 10, wherein the electrically conductive layer is deposited to have a thickness of 5-25 microns.

14. The method as in claim 10, wherein the electrically insulating layers are each deposited at a thickness of less than 100 microns, and the electrically conductive layer is deposited to have a thickness of less than 25 microns.

15. The method as in claim 10, wherein the step of depositing an electrically conductive layer comprises at least one of the group of plasma spraying, electron beam physical vapor deposition (EB PVD), chemical vapor deposition (CVD), pulsed laser deposition, mini-plasma, cold spray, direct-write, mini-high velocity oxyfuel, and solution plasma spraying of an electrically conductive material.

* * * * *